United States Patent
Lin et al.

(10) Patent No.: US 11,139,068 B2
(45) Date of Patent: Oct. 5, 2021

(54) METHODS, SYSTEMS, AND COMPUTER READABLE MEDIA FOR SMART IMAGE PROTOCOLING

(71) Applicant: The University of North Carolina at Chapel Hill, Chapel Hill, NC (US)

(72) Inventors: Weili Lin, Chapel Hill, NC (US); Dinggang Shen, Chapel Hill, NC (US); Jeffrey Keith Smith, Sanford, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 40 days.

(21) Appl. No.: 16/329,622

(22) PCT Filed: Nov. 6, 2017

(86) PCT No.: PCT/US2017/060236
§ 371 (c)(1),
(2) Date: Feb. 28, 2019

(87) PCT Pub. No.: WO2018/085788
PCT Pub. Date: May 11, 2018

(65) Prior Publication Data
US 2019/0228857 A1 Jul. 25, 2019

Related U.S. Application Data (60) Provisional application No. 62/418,128, filed on Nov. 4, 2016.

(51) Int. Cl.
*G06K 9/00* (2006.01)
*G16H 30/40* (2018.01)
(Continued)

(52) U.S. Cl.
CPC .......... *G16H 30/40* (2018.01); *G06F 16/583* (2019.01); *G06N 20/00* (2019.01); *G06T 7/0012* (2013.01);
(Continued)

(58) Field of Classification Search
CPC .................. G06F 16/583; G06N 20/00; G06T 2207/10016; G06T 2207/10081;
(Continued)

(56) References Cited

U.S. PATENT DOCUMENTS

2014/0180063 A1* 6/2014 Zhao .................... A61B 1/0005
600/424
2015/0011401 A1* 1/2015 Davicioni ............. C12N 15/111
506/2
(Continued)

OTHER PUBLICATIONS

Notification of Transmittal of the International Search Report and the Written Opinion of the International Searching Authority, or the Declaration for International Application Serial No. PCT/US2017/060236 (dated Feb. 21, 2018).

*Primary Examiner* — Xin Jia
(74) *Attorney, Agent, or Firm* — Jenkins, Wilson, Taylor & Hunt, P.A.

(57) ABSTRACT

A method for smart image protocoling includes, using a medical imaging device, obtaining, using a first medical imaging sequence, a first set of medical images of a patient. Anatomical and, if present, disease features are extracted from the first set of medical images. A machine learning trained algorithm is used to determine, in real time, and based on the extracted anatomical and/or disease features, whether a desired medical imaging goal is achieved for the patient. In response to determining that the desired medical imaging goal is achieved, at least one image from the first set of medical images is output as a final image. In response to determining that the desired medical imaging goal has not (Continued)

been achieved, the machine learning trained algorithm is used to select a second medical imaging sequence. A second set of medical images of the patient is obtained using the second medical imaging sequence. The above outlined procedures will be repeated until the final imaging goal is achieved for a patient.

18 Claims, 6 Drawing Sheets

(51) Int. Cl.
*G16H 40/63* (2018.01)
*G16H 50/70* (2018.01)
*G06F 16/583* (2019.01)
*G06N 20/00* (2019.01)
*G06T 7/00* (2017.01)

(52) U.S. Cl.
CPC ............ *G16H 40/63* (2018.01); *G16H 50/70* (2018.01); *G06T 2207/10016* (2013.01); *G06T 2207/10081* (2013.01); *G06T 2207/10088* (2013.01); *G06T 2207/10104* (2013.01); *G06T 2207/20081* (2013.01)

(58) Field of Classification Search
CPC . G06T 2207/10088; G06T 2207/10104; G06T 2207/20081; G06T 7/0012; G16H 30/40; G16H 40/63; G16H 50/70
See application file for complete search history.

(56) References Cited

U.S. PATENT DOCUMENTS

2016/0022238 A1* 1/2016 Park .................... G06T 7/0012
                                                                600/410
2016/0058426 A1   3/2016 Hedlund et al.
2017/0103287 A1* 4/2017 Han ...................... G06N 20/00

* cited by examiner

Fig. 1

Fig. 2 Conventional and widely used approaches

Fig. 3 An automated method to select protocol

Fig 4: The proposed approach

METHODS, SYSTEMS, AND COMPUTER READABLE MEDIA FOR SMART IMAGE PROTOCOLING

PRIORITY CLAIM

This application claims the priority benefit of U.S. Provisional Patent Application Ser. No. 62/418,128, filed Nov. 4, 2016, the disclosure of which is incorporated herein by reference in its entirety.

TECHNICAL FIELD

The subject matter described herein relates to medical imaging. More particularly, the subject matter described herein relates to methods, systems, and computer readable media for smart image protocoling.

BACKGROUND

Figure 1:
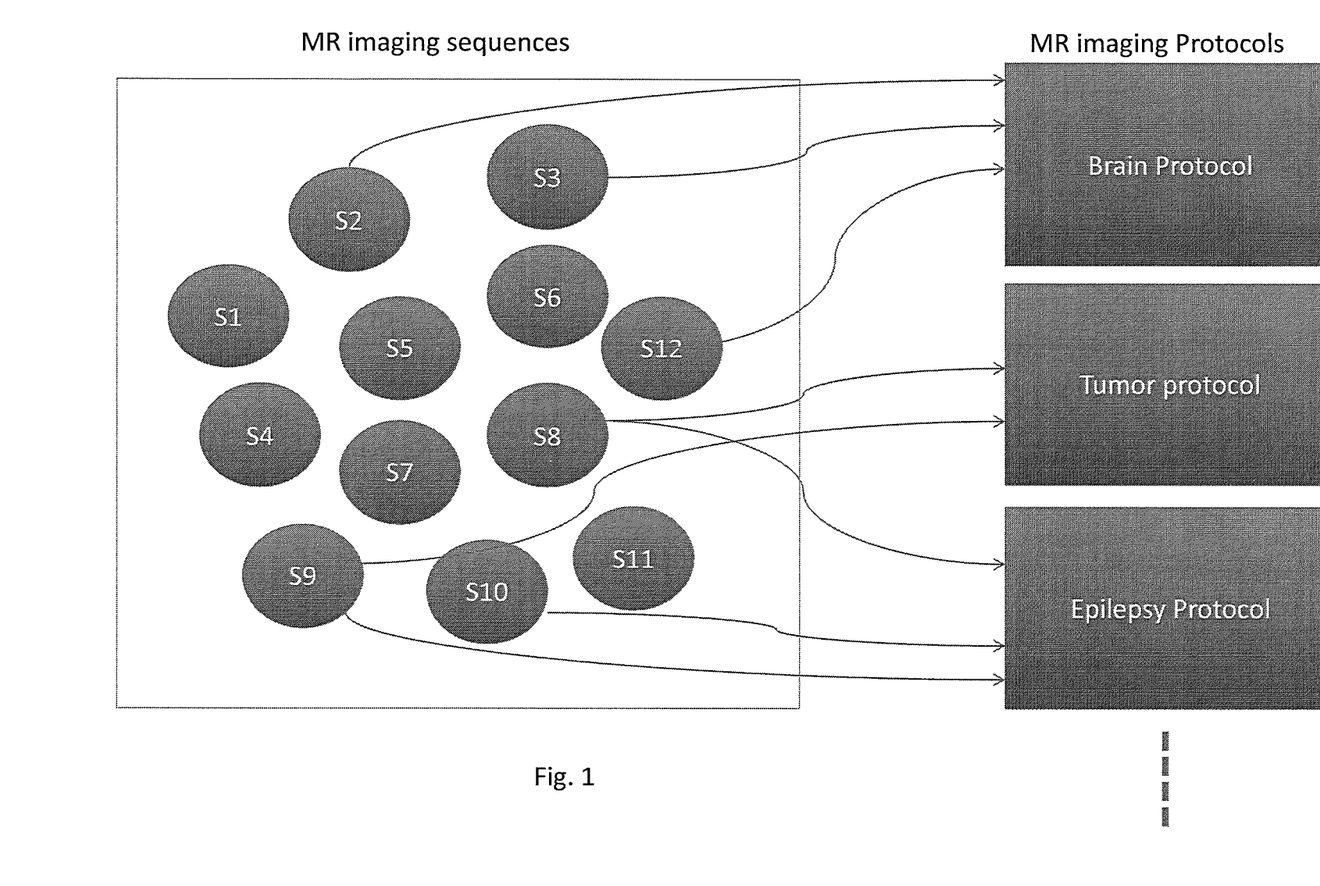
FIG. 1 is a diagram of MR imaging sequences and MR imaging protocols.

Medical imaging, such as magnetic resonance imaging (MRI), is typically performed according to a fixed protocol depending on a patient's initial diagnosis. The term "protocol", as used herein, refers to a set of pre-determined MR imaging sequences acquiring MR images with different contrast, orientation, imaging parameters and even different physiological information (FIG. 1). For example (FIG. 2), a patient complaining of headaches may receive a brain MRI protocol, consisting of a set of MR imaging sequences that are deemed by radiologists to provide relevant radiological information for them to make clinical diagnosis. When the acquired brain MRI subsequently reviewed by a radiologist, if the brain MRI reveals a brain mass, suggestive of a brain tumor, the patient may be called for an additional office visit to have more detailed magnetic resonance imaging. Specifically, a dedicated brain tumor MR imaging protocol will then be used at the second visit (FIG. 1). Such a manual process is inefficient because it requires expert judgment on the part of the radiologist, manual reading of the initial image, and multiple office visits for the patient.

Figure 3:
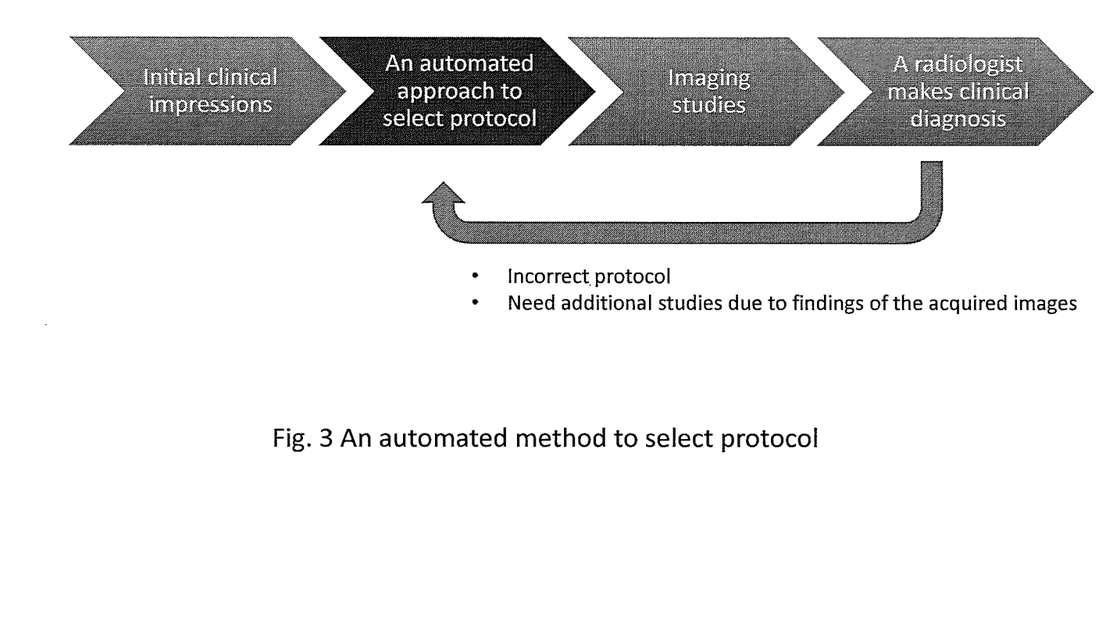
FIG. 3 a diagram of an automated method to select a protocol.

Alternatively, imaging protocol recommender devices that automatically recommend imaging protocol sequences have been described (FIG. 3). However, while some of such devices may provide recommendations for a radiologist, the devices still require expert judgment and multiple patient visits for subsequent scans. Specifically, this approach basically aims to replace a radiologist making a selection of protocol based on some clinical information. As a result, it remains possible that a patient receiving a brain MR protocol could reveal a brain mass and subsequently requires an additional study using the dedicated brain tumor protocol. Other imaging protocols utilize a scout scan before determining whether to perform a more detailed scan. However, even such systems require expert judgment and analysis of the scout scan and may still require multiple patient office visits.

Accordingly, there exists a need for methods, systems, and computer readable media for smart image protocoling.

SUMMARY

A method for smart image protocoling will mitigate the problems encountered with the currently available approaches. The smart protocoling will not select MR imaging studies from a set of pre-determined protocols (FIG. 1). Instead we will start with a pre-selected sequence that can be chosen based on the medical history and clinical information of a specific patient or a sequence that is commonly used for the organ of interest as a starting point to acquire a set of MR images. Using these images, a machine learning trained algorithm is used to determine, in real time, and based on the extracted anatomical and/or disease features, to determine the next MR imaging sequence. The above processes will then be repeated until a desired medical imaging goal is achieved for the patient.

A system for smart image protocoling includes an imaging sequence controller for controlling an imaging sequence implemented by a medical imaging device or researchers operating such a device. The imaging sequence controller includes at least one processor and a memory. A feature extractor extracts, in real time, anatomical and, if present, disease features from a first set of medical images obtained using the medical imaging device. The term "set of medical images", as used herein, may include one or more medical images. An imaging sequence selector uses a machine learning trained algorithm to determine, in real time, and based on the extracted anatomical and/or disease features, whether a desired medical imaging goal is achieved for the patient. In response to determining that the desired medical imaging goal is achieved, the imaging sequence selector will stop the imaging session and output all or a subset the medical images. In response to determining that the desired medical imaging goal has not been achieved, the imaging sequence selector selects, using the machine learning trained algorithm a second medical imaging sequence and obtains, in real time, a second set of medical images of the patient using the second medical imaging sequence.

As used herein, applying imaging sequences and extracting features in real time means, in one example, that the imaging sequences and feature extraction can be applied back to back, with little or no delay between imaging applications. Applying imaging sequences and feature extractions in real time reduces the need for multiple office visits for the patient solely for the purpose of applying different imaging sequences, utilizes a set of imaging sequences tailored to each patient's clinical indication, and potentially, reduces study time and avoids unnecessary contrast agent.

According to another aspect of the subject matter described herein, the medical imaging device comprises a magnetic resonance imaging device, which acquires an initial magnetic resonance imaging sequence selected based on a patient's medical history or an imaging sequence that is commonly used for an organ of interest. A second medical imaging sequence may subsequently be acquired, where the second medical imaging sequence comprises a magnetic resonance imaging scan sequence with at least one of an orientation, slice thickness, resolution, contrast, and spatial coverage selected based on features extracted from the initial magnetic resonance imaging sequence.

The subject matter described herein may be implemented in hardware, software, firmware, or any combination thereof. As such, the terms "function", "node" or "module" as used herein refer to hardware, which may also include software and/or firmware components, for implementing the feature being described. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

The subject matter described herein will now be explained with reference to the accompanying drawings of which.

DETAILED DESCRIPTION

Although the proposed concept can be extended to, potentially, broader applications, we will start by focusing on one specific area, magnetic resonance imaging (MRI). A separate section will further elaborate how the proposed approach can be expanded to broader applications.

Smart MR Imaging Protocols (or Individualized MR Imaging Protocol)

Currently, a wide array of MR imaging protocols is pre-defined for different diseases (FIG. 1). For example, for neurological diseases, there are protocols for epilepsy, stroke, multiple sclerosis, and so on. Under each disease category, the protocols are further divided into pediatric or adult patients. Each imaging protocol consists of a collection of MR imaging sequences aiming to obtain different tissue contrasts, orientations, imaging resolution, coverage, and so on (FIG. 1). In addition, some of the protocols include the injection of MR contrast agent and acquiring additional images post-contrast.

Figure 2:
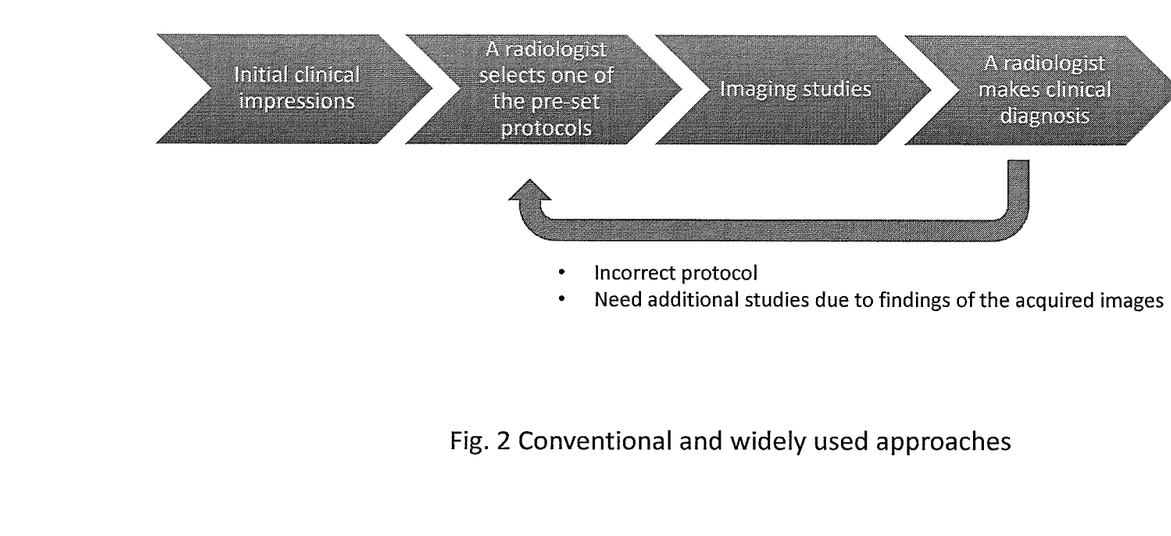
FIG. 2 is a diagram of a conventional imaging protocol.

When a diagnostic MR is ordered by a clinician, several different approaches have been utilized by different imaging centers to select a specific MR imaging protocol. At one medical center, radiologists determine what the MR protocol to be used based on the medical history and clinical indications (FIG. 2). Subsequently, a MR protocol is selected. In contrast, at many imaging sites, radiologists do not perform this review and protocoling process. The MR imaging protocol may be selected by a technologist or ordering provider, with a relatively small menu of choices (e.g. routine brain, pituitary, internal auditory canal (IAC), tumor, stroke protocols). The ordering provider usually has limited knowledge about the scanner protocols. The radiology technologist may have limited knowledge of medical symptoms or diagnoses, and/or limited access to patient medical records. The information is entered into the requisition form for a MR technologist who will then select the specific protocol and run the set of MR sequences pre-compiled for the patients.

There are several major limitations associated with this current approach.

1. The imaging protocol is not individualized as each patient is different even if they are in the same disease category. A simple example would be brain tumor patients where the sizes and locations of tumors differ between patients.

2. While medical history and presumed clinical indications provide a rational basis for protocol selection, they do not necessarily offer the most accurate information. It is plausible that medical history and presumed clinical indications do not result in correct protocol selection, leading to an additional imaging session. In many cases there is an opportunity to substantially alter the patient's diagnosis during the imaging session—for example a patient may have a brain MRI ordered based on headache and confusion, but the first images acquired may reveal a brain mass, suggesting the diagnosis of brain tumor. There is an opportunity to act on this information to provide real time personalized and individually optimized scan sequences, such as adding post contrast images or additional 3D volume acquisition optimal for brain tumor treatment planning.

3. It requires an expert physician with knowledge of imaging (e.g. a radiologist) to protocol each requested imaging study for each patient. This is time consuming and often difficult or time consuming to obtain and review all relevant clinical information. In the sites where radiologists do not involve in protocoling, the chances of patients not receiving optimal imaging protocols are high, leading to additional costs of re-scanning.

4. It has been well documented that MR contrast agents may lead to nephrogenic systemic fibrosis (NSF) for patients with compromised kidney function. More recently, it has been suggested that free gadolinium (Gd) may be deposited in the brain. Currently, the need of administering gadolinium containing MR contrast agent is determined based on clinical indications prior to imaging studies. Smart protocoling as proposed here will take into consideration the images acquired during imaging session and determine whether a contrast agent is indeed needed. Administering contrast agents only in cases where imaging findings or clinical information suggest a high yield for additional useful information would allow optimal risk/benefit in an individualized manner for each patient.

5. Lack consistency across patients, ordering providers and radiologist.

Figure 4:
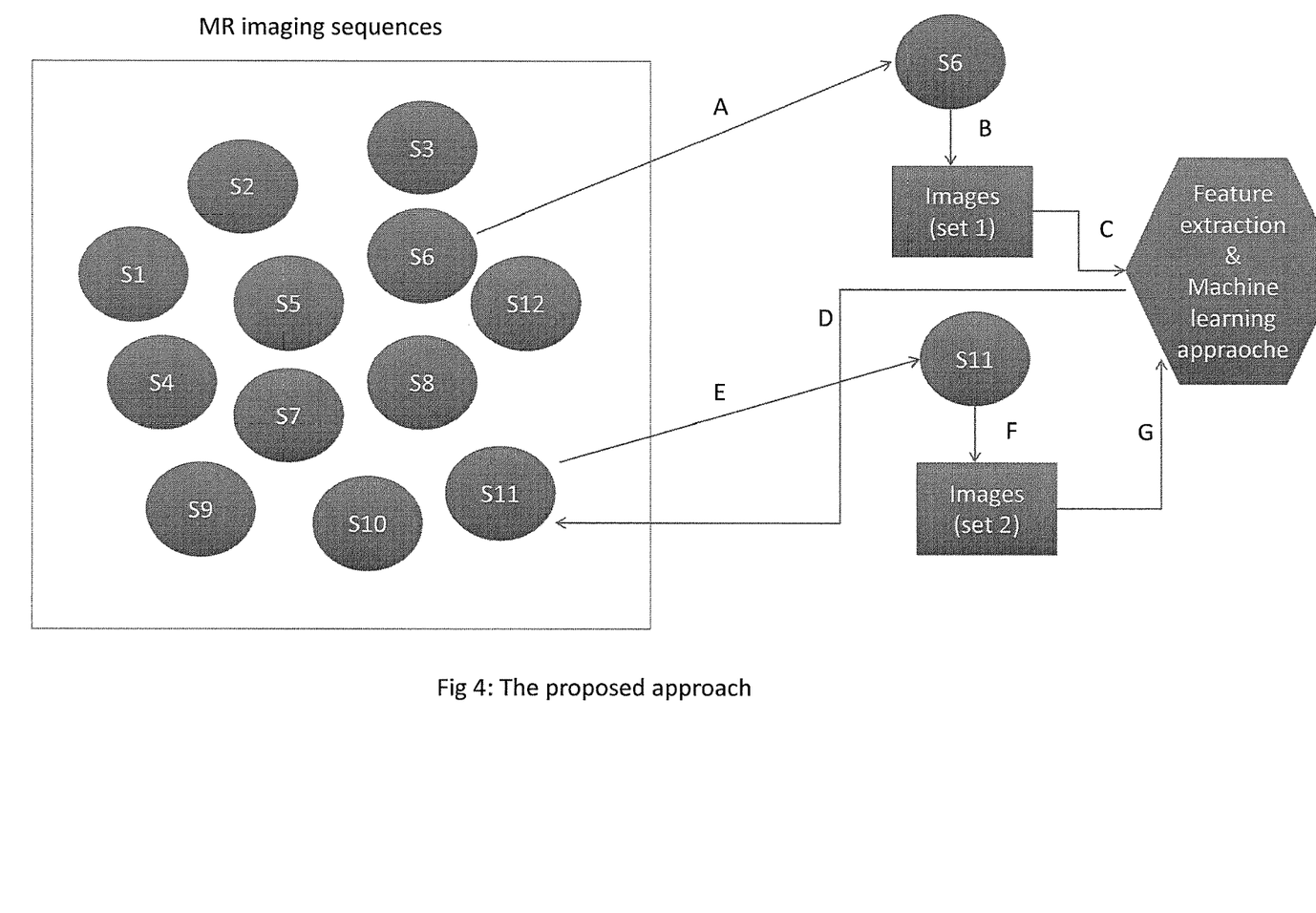
FIG. 4 is a diagram of a method for smart image protocoling according to an embodiment of the subject matter described herein.

Our proposed concept is to leverage innovative machine learning approaches to develop "smart MR imaging protocol" that in essence 1) eliminates the need for radiologists or technologists to protocol for each patient, 2) automatically selects initial MR imaging sequences for each patient, 3) selects additional imaging sequences regarding contrast as well as imaging parameters on the fly based on findings from the initial MR imaging sequences and clinical information, 4) ensures consistency in imaging acquisition across patients with the same clinical indication, 5) determine whether or not contrast agent is indeed needed and 6) determine if abbreviate imaging protocols should be used in the event when patients exhibit substantial motion artifacts Methods To achieve the above goal of achieving smart MR imaging protocoling for each individual patient, the flowchart of our approach is provided in FIG. 4.

Step A: A sequence will be pre-selected based on either a patient's clinical indications and/or medical history or a commonly used sequence for specific organ. In the figure, S6 is chosen as the first imaging sequence for example.

Step B: The chosen sequence will acquire a set of images.

Step C: The acquired images will then be fed to the machine-learning platform to be discussed below.

Step D: Based on the results from the machine-learning platform, a different sequence is then chosen, (S11 for example).

Step E: The chosen S11 sequence will then be used.

Step F: The second set of images will be acquired.

Step G: The second set of images will be fed to the machine-learning platform again. The first and second image data sets will then be jointly used for determining the third sequence.

These processes will be repeated until the final diagnosis is reached.

Machine Learning

We will use the machine learning techniques to determine what the optimal MR imaging protocol for each individual patient using images, lab results, demographic information, and medical history from existing patients. Both training and testing stages are described below.

In the training stages, for each category of disease and age (i.e., pediatric or adult), we will first collect a large set of cases from our picture archive and communication system (PACS) system, which is a repository that stores medical image sequences and corresponding clinical interpretations of the image sequences. We will then train specific learning the values of each imaging sequence. (1) First, based on clinical interpretations by clinicians, such as radiologists, we know which imaging sequences are finally critical for diagnosis of disease for each particular patient. For example, some sequences must be used based on clinical information only, e.g., if patient has stroke like symptoms, we would always want diffusion weighted imaging (DWI). Similarly, if patient has cranial nerve deficit, we would always want post contrast images and thin section skull base images. In another example, if a patient has fever or known malignancy, we always want image sequences in which contrast agents are used to enhance anatomical or disease features of interest. That is, in this way, we can collect a large set of cases, each with its optimal combination of imaging sequences, and thus obtain a training database, summarizing different combinations of imaging sequences that are effective to diagnosis of disease for a specific category of patients (with category of disease and age). (2) Then, based on this database, we can construct a tree to optimally cover all cases in the training database and also describe the order of scanning after each previous set of images becoming available.

Using neurological diseases as the example, the root of tree can include two main imaging sequences often ordered for each patient, i.e., 3D T1-weighted and 3D T2-weighted sequences that cover the entire brain. Each node in the tree denotes a different imaging modality to scan. Thus, the path from the root of the constructed tree to each leaf node will cover a possible combination of imaging modalities appeared in the training database. By minimizing the overall paths from the root (with 3D T1-weighted and 3D T2-weighted sequences) to the leaf nodes in the tree, we can build a tree, which provides different possible choices of sequences after obtaining images from the first two initial T1 and T2 images in the parent nodes. (3) Next, we can train one machine learning model for each node in the tree to learn which candidate path should be selected according to the previously acquired imaging modalities, by using both the constructed trees and all examples in the training database. Specifically, by extracting features from all the previous images, we can train a particular machine learning model to predict which child node to select (equally, which next imaging sequence to scan) based on the respective training examples in the training database. Note that, for all respective examples in the training database, we know what the next imaging sequence is used to scan, given the previous scanned imaging sequences; thus, we can use this information to optimize all the parameters in our machine learning model. With this proposed training method, we can train one machine learning model for each node in the tree, thus offering the capability of selecting a next child node in the tree or selecting a next imaging sequence to scan. With the sufficient examples obtained from our PACS system, we expect to have very promising results for smart active imaging protocol selection for all examples in the training dataset.

In the testing step or application stage, again using MR as the modality and neurological diseases as an example, we will first use a MR imaging sequence based on the medical history and clinical information or a commonly used sequence based on the organ of interest. For example, 3D T1-weighted imaging sequence covering the entire brain for brain imaging for the new patient, and then predict the next imaging sequence to scan based on the trained model stored in the root of tree. After scanning using the newly selected sequences, the available images combine with the previous scanned images (i.e., T1 MRI), we can extract their features and then use the trained model scored in the current node to predict the next new imaging sequence to scan. By repeating this process, we can reach a certain leaf node of the tree, and thus all imaging sequences in the selected path from the root to the reached leaf of tree will be acquired for the current patient. An example of workflow for MR imaging of patients with neurological diseases will now be described:

We will first take all of the available information from the patients, including but not limit to clinical indications, medical history, lab results, demographic information, prior images if availability, and results from other imaging modalities if available prior to the scheduled imaging sessions into the developed machine learning approaches and select a set of candidate sequences.

We will acquire one main sequence for all patients: 3D T1-weighted. The sequence will cover the entire brain.

Images obtained from the sequence will be entered into the machine learning platform to select the second sequence. In addition, the imaging parameters, including but not limited to orientations, slice thicknesses, resolution, spatial coverage and so on, will also be automatically determined based on the findings from the first two sequences.

Information learned from the second sequence will then be used to select the third sequence and so on until the needed information is collected for clinical diagnosis.

Furthermore, the proposed approaches will also determine if contrast agent will be needed based on the information learned from the acquired images and clinical data.

If contrast agent is needed, the MR technologist will be prompt with the information.

In addition to the above procedure, we will also build in real-time image quality check. If the acquired images exhibit substantial motion artifacts, the information will be integrated to modify imaging parameters by compromising image resolution while reducing acquisition time.

Potential Impacts

Individualized protocoling for each patient to maximize diagnostic accuracy and minimize risk and time spent in scanner.

Individualized protocoling to minimize costs associated with the need of a radiologist for protocoling and/or patient recall.

Automated protocol/sequence selection will alleviate the workload for technologists.

Individualized protocoling for each patient to avoid additional scans due to findings in the prior scan, reducing healthcare costs.

Individualized protocoling for each patient could reduce the chance of patients receiving unnecessary contrast agent.

The developed approaches could also lead to a reduction in radiologist workload potentially.

The impacts can potentially be even greater for small medical centers and/or private practices.

The developed approaches could allow the design of temporal sequence of choosing different imaging modalities if a patient needs multiple imaging studies such that if adequate clinical information is obtained, the remaining imaging modalities can be stopped even they have not been obtained A Broader Possibility of the Proposed Concept The above discussion narrowly focused on MR applications only. However, the same concept can be further expanded to design imaging protocol including different imaging modalities such as MRI, positron emission tomography (PET), computed tomography (CT), and ultrasound. For example, in many cases, patients undergo not only one imaging modality but multiple imaging sessions since each modality provides different clinical information. Therefore, the proposed concept can be expanded to design different paths for each patient where each path will have different combinations of imaging modalities. The composition of each path will be adjusted when images from other modalities become available.

Figure 5:
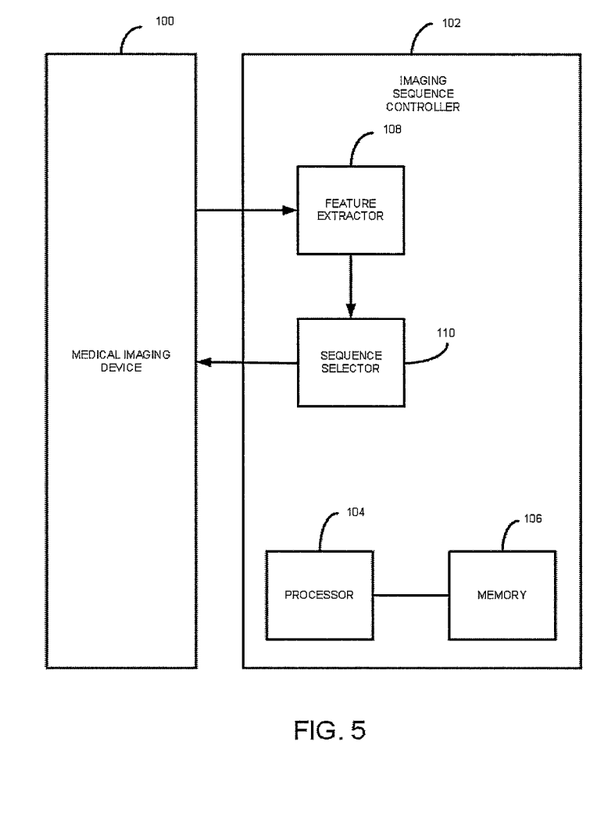
FIG. 5 is a block diagram of a system for smart image protocoling according to an embodiment of the subject matter described herein.

FIG. 5 is a block diagram of a system for smart image protocoling according to an embodiment of the subject matter described herein. Referring to FIG. 5, the system includes a medical imaging device 100 that is capable of obtaining medical images of a patient. The medical imaging device may be a magnetic resonance imaging device, a PET imaging device, a CT imaging device, an ultrasound imaging device, or any combination of two or more of these imaging devices. An imaging sequence controller 102 may be coupled to medical imaging device 100 to control the sequence of images captured or obtained by the medical imaging device. Controller 102 may be integrated within medical imaging device 100 or may be implemented at least in part on a computing platform separate from the medical imaging device. Controller 102 may include a processor 104 and memory 106.

In the illustrated example, controller 102 includes a feature extractor 108 for extracting anatomical structures and/or disease structures from medical images in real time. In addition, controller 102 may include an imaging sequence selector 110 for selecting an imaging sequence based on features extracted by feature extractor 108 and for controlling, in real time, medical imaging device 100 to implement the selected imaging sequence. Imaging sequence selector 110 may implement the machine-learning trained decision tree described above. The process of obtaining medical images, extracting features, selecting new imaging sequence, and obtaining the new imaging sequences may be performed recursively and in real time to repeatedly update the imaging sequence being performed for a particular patient according to the features extracted during each scan until a desired imaging goal is achieved. The desired imaging goal may include reaching a leaf node in the decision tree described above, where the leaf node corresponds to a particular clinical diagnosis. Such a system may avoid multiple patient office visits and produce a set of medical images that is tailored to the individual patient's condition.

Figure 6:
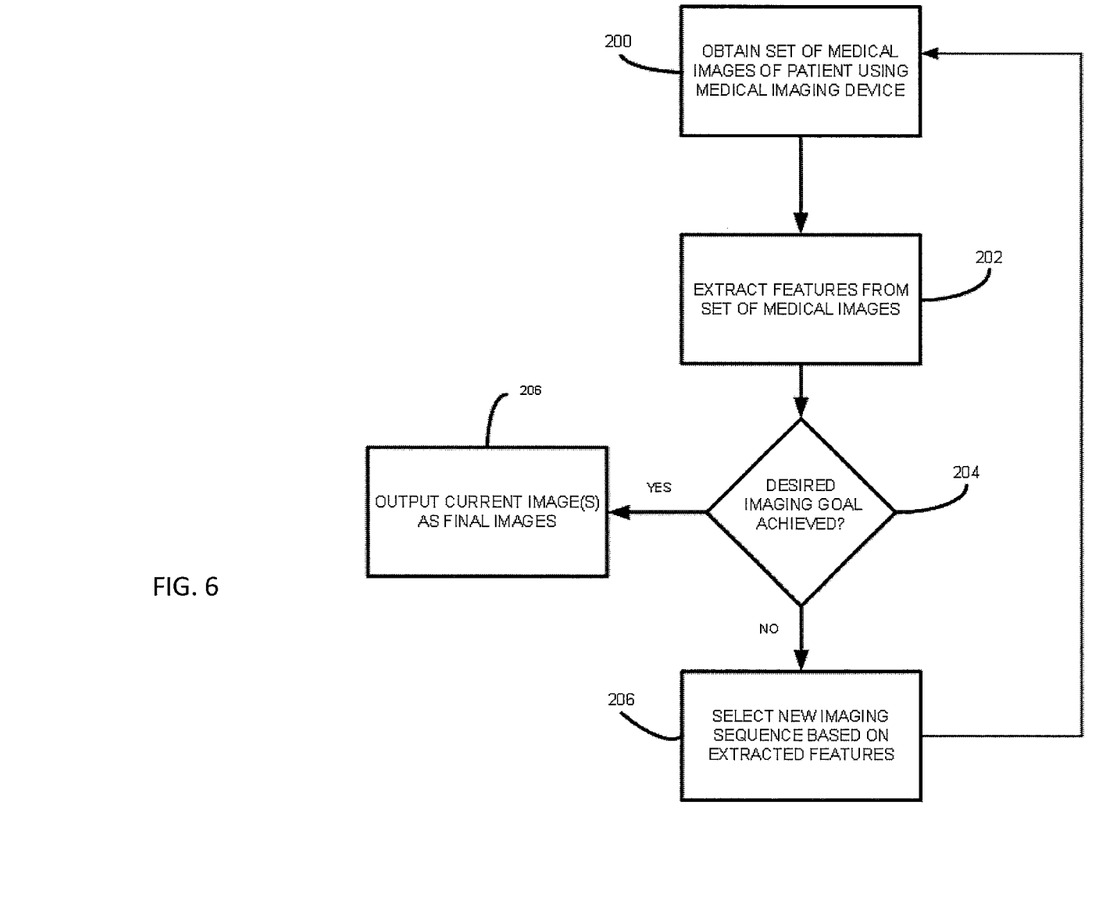
FIG. 6 is a flow chart of a process for smart image protocoling according to an embodiment of the subject matter described herein.

FIG. 6 is a flow chart illustrating exemplary overall steps for smart image protocoling according to an embodiment of the subject matter described herein. Referring to FIG. 6, in step 200, a medical imaging device is used to obtain a set of medical images of a patient. The medical imaging device may be any of the medical imaging devices described above. The set of medical images that is obtained may be based on an initial medical imaging for a patient's initial or suspected diagnosis.

In step 202, features are extracted from the set of medical images. The features may be extracted automatically by feature extractor 108. The features may be anatomical features of the patient, disease features, or a combination thereof. Feature extraction may be performed automatically by identifying potential structures in medical images and comparing the potential structures to a database or atlas of known features. Once the features are extracted, in step 204, it is determined whether a desired imaging goal has been achieved. Step 204 may be performed by applying the extracted features from the medical imaging sequence in step 200 to the above-described machine learned decision tree, where at each node in the tree, a decision is made related to the patient's diagnosis. If a leaf node indicating that the patient is normal is reached, control may proceed to step 206 where the current set of medical images is output as the final set of images, and no further imaging may be required.

If, on the other hand, the result of applying the extracted features to the decision tree is that the desired imaging goal has not been achieved by the current set of medical images, control proceeds to step 206 where a new imaging sequence is selected based on the extracted features. For example, the extracted features may be applied to the machine learned decision tree. At each node in the decision tree, the algorithm determines whether to proceed down a left hand or a right hand branch based on decisions associated with each node. Once the new imaging sequence is selected, control returns to step 200 where at least one medical image is obtained using the newly selected sequence. Steps 200, 202, 204, and 206 can be repeated recursively until a desired imaging goal has been met.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for smart image protocoling comprising:
extracting anatomical or disease features from the first set of medical images;
using a machine learning trained algorithm to determine, based on the extracted anatomical or disease features, that a desired medical imaging goal is not achieved from the first medical imaging sequence for the patient, wherein the machine learning trained algorithm is trained using a repository of medical image sequences and corresponding clinic interpretations of the medical image sequences to select, given features extracted from the medical images, a sequence of medical images that is optimal for patient-specific diagnosis of a disease; and in response to determining that the desired medical imaging goal is not achieved from the first medical imaging sequence, selecting, using the machine learning trained algorithm a second medical imaging sequence and obtaining a second set of medical images of the patient using the second medical imaging sequence, wherein the first and second medical imaging sequences are clinical diagnostic medical imaging sequences and wherein the second medical imaging sequence is performed using at least one different medical imaging parameter from the first medical imaging sequence.

2. The method of claim 1 using the machine learning trained algorithm comprises applying the extracted features to a decision tree.

3. The method of claim 1 comprising extracting features from the second set of medical images, using the machine learning trained algorithm to determine, in real time, and based on the extracted features from the first set of medical images and the second set of medical images, whether the desired medical imaging goal is achieved for the patient, in response to determining that the desired medical imaging goal is achieved, outputting at least one image from the first and second sets of medical images, and, in response to determining that the desired medical imaging goal has not been achieved, selecting, using the machine learning trained algorithm, a third medical imaging sequence, and obtaining, in real time, a third set of medical images of the patient using the third medical imaging sequence.

4. The method of claim 1 wherein the medical imaging device comprises a magnetic resonance imaging device, the first medical imaging sequence comprises an initial magnetic resonance imaging sequence selected based on a patient's medical history or an imaging sequence for an organ of interest and wherein the second medical imaging sequence comprises a magnetic resonance imaging scan sequence with at least one of an orientation, slice thickness, resolution, contrast, and spatial coverage selected based on features extracted from the initial magnetic resonance imaging sequence.

5. The method of claim 1 comprising recursively obtaining medical images of the patient, extracting features from the medical images, and updating a medical imaging sequence for obtaining the medical images until the desired imaging goal is achieved.

6. The method of claim 1 wherein selecting the second medical imaging sequence includes selecting an imaging modality for the second medical imaging sequence.

7. The method of claim 6 wherein the modality for the second medical imaging sequence is different from an imaging modality of the first medical imaging sequence.

8. The method of claim 1 wherein the extracting, determining, and obtaining occur in real time.

9. A system for smart image protocoling, the system comprising:

an imaging sequence controller for controlling an imaging sequence implemented by a medical imaging device, the imaging sequence controller including:
at least one processor;
a memory;
a feature extractor for extracting anatomical or disease features from a first set of medical images of a patient obtained by the medical imaging device using a first medical imaging sequence; and an imaging sequence selector for:
using a machine learning trained algorithm to determine based on the extracted anatomical and/or disease features, that a desired medical imaging goal is not achieved from the first medical imaging sequence for the patient, wherein the machine learning trained algorithm is trained using a repository of medical image sequences and corresponding clinical interpretations of the medical image sequences to select, given features extracted from medical images, a sequence of medical images that is optimal for patient-specific diagnosis of a disease; and in response to determining that the desired medical imaging goal is not achieved from the first medical imaging sequence, selecting, using the machine learning trained algorithm a second medical imaging sequence and obtaining a second set of medical images of the patient using the second medical imaging sequence, wherein the first and second medical imaging sequences are clinical diagnostic medical imaging sequences and wherein the second medical imaging sequence is performed using at least one different medical imaging parameter from the first medical imaging sequence.

10. The system of claim 9 wherein the medical imaging device comprises a magnetic resonance imaging device, a computed tomography imaging device, or a positron emission tomography imaging device.

11. The system of claim 10 wherein the machine learning trained algorithm is implemented as a decision tree.

12. The system of claim 10 wherein the feature extractor is configured to extract features from the first and second sets of medical images and wherein the imaging sequence selector is configured to use the machine learning trained algorithm to determine, in real time, and based on the extracted features from the first and second sets of medical images, determine whether the desired medical imaging goal is achieved for the patient, in response to determining that the desired medical imaging goal is achieved, output at least one image from the first and second sets of medical images, in response to determining that the desired medical imaging goal has not been achieved, select, using the machine learning trained algorithm a third medical imaging sequence, and obtain, in real time, a third set of medical images of the patient using the third medical imaging sequence.

13. The system of claim 10 wherein the medical imaging device comprises a magnetic resonance imaging device, the first medical imaging sequence comprises an initial magnetic resonance imaging sequence selected based on a patient's medical history or an imaging sequence for an organ of interest and wherein the second medical imaging sequence comprises a magnetic resonance imaging scan sequence with at least one of an orientation, slice thickness, resolution, contrast, physiological information, and spatial coverage selected based on features extracted from the initial magnetic resonance imaging sequence.

14. The system of claim 10 wherein the imaging controller is configured to recursively obtain medical images of the patient, extract features from the medical images, and update a medical imaging sequence for obtaining the medical images until the desired imaging goal is achieved.

15. The system of claim 10 wherein selecting the second medical imaging sequence includes selecting an imaging modality for the second medical imaging sequence.

16. The system of claim 15 wherein the modality for the second medical imaging sequence is different from an imaging modality of the first medical imaging sequence.

17. The system of claim 10 wherein the extracting, determining, and obtaining occur in real time.

18. A non-transitory computer readable medium having stored thereon executable instructions that when executed by the processor of a computer control the computer to perform steps comprising:

using a medical imaging device, obtaining, using a first medical imaging sequence, a first set of medical images of a patient;

extracting anatomical and, if present, disease features from the first set of medical images;

using a machine learning trained algorithm to determine, based on the extracted anatomical and/or disease features, that a desired medical imaging goal is not achieved from the first medical imaging sequence for the patient, wherein the machine learning trained algorithm is trained using a repository of medical image sequences and corresponding clinical interpretations of the medical image sequences to select, given features extracted from medical images, a sequence of medical images that is optimal for patient-specific diagnosis of a disease; and in response to determining that the desired medical imaging goal is not achieved from the first medical imaging sequence, selecting, using the machine learning trained algorithm, a second medical imaging sequence and obtaining, a second set of medical images of the patient using the second medical imaging sequence, wherein the first and second medical imaging sequences are clinical diagnostic medical imaging sequences and wherein the second medical imaging sequence is performed using at least one different medical imaging parameter from the first medical imaging sequence.

* * * * *